United States Patent [19]

Simms

[11] 4,029,420
[45] June 14, 1977

[54] LIGHT REFLECTANCE INSTRUMENT

[76] Inventor: Romilly John Simms, 2192 Clayton Drive, Menlo Park, Calif. 94025

[22] Filed: Dec. 27, 1974

[21] Appl. No.: 536,715

[52] U.S. Cl. .................................. 356/209; 26/70; 356/210; 356/238
[51] Int. Cl.² ............... G01N 21/48; G01N 21/16; G01N 21/32
[58] Field of Search .......... 356/209, 210, 211, 212, 356/238; 250/571, 572; 26/70

[56] References Cited
UNITED STATES PATENTS

| | | | |
|---|---|---|---|
| 2,321,722 | 6/1943 | Zelony | 356/212 |
| 2,882,785 | 4/1959 | Biesele, Jr. | 356/212 |
| 3,512,894 | 5/1970 | Wood | 356/209 |
| 3,554,656 | 1/1971 | Eicken | 356/238 |
| 3,782,836 | 1/1974 | Fey et al. | 356/209 |
| 3,846,027 | 11/1974 | Hyman et al. | 356/210 |

Primary Examiner—Vincent P. McGraw
Attorney, Agent, or Firm—Lowhurst & Aine

[57] ABSTRACT

An instrument for measuring light reflectance from fabric and the like materials which have a heterogeneous surface configuration includes an aperture defining a sensing area, three light sources for illuminating the sensing area, and a photoelectric cell for detecting light reflected from the material in the sensing area. The light sources are mounted at 120° with respect to one another around an outer periphery of the cell. The cell is mounted coaxially with respect to and a spaced distance from the aperture. Each light source is mounted on a line which passes through the center of the aperture and is at an angle of 30° with respect to an axis of the aperture.

7 Claims, 3 Drawing Figures

U.S. Patent  June 14, 1977  4,029,420
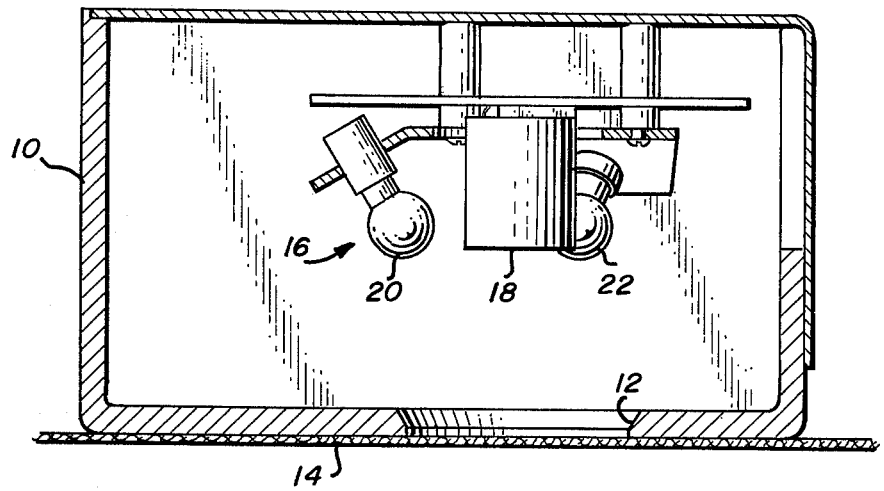
Fig_1
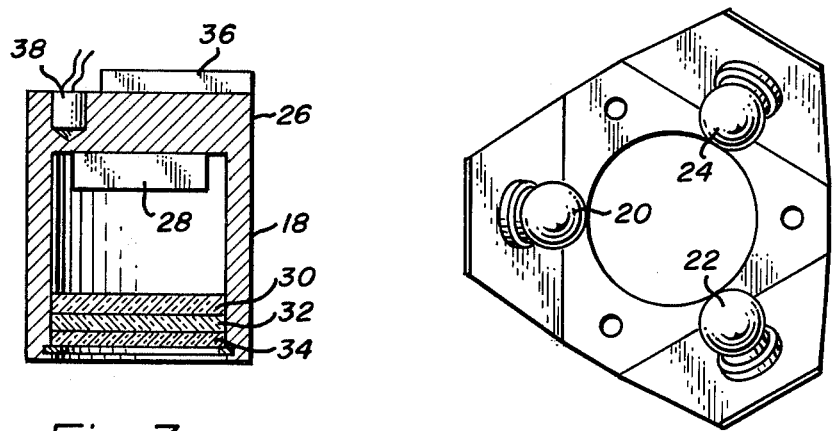
Fig_3
Fig_2

LIGHT REFLECTANCE INSTRUMENT

BACKGROUND OF THE INVENTION

1. Field of the Invention

This invention relates generally to an instrument for measuring light reflectance from a surface, and more particularly to such an instrument for measuring light reflectance from fabric and the like materials which have a heterogeneous surface configuration.

2. Prior Art

A number of instruments are presently available for measuring light reflectance from a surface. Generally, such instruments employ a single light source and a single light sensor mounted with respect to one another such that the sensor will receive only diffused light from the surface under investigation. Usually this is accomplished by mounting a light sensor on a line which is normal to the surface under investigation and a light source on a line which is at 45° with respect to the normal. Of course, the light source and the light sensor can be interchanged in their positions to obtain the same effect.

However, this arrangement is not satisfactory for investigating the light reflectance of materials having a heterogeneous surface configuration, such as fabrics. The problems encountered with fabrics are caused by the heterogeneous surface configuration thereof consisting of overlapping and intertwined threads or fibers. Modern fabrics, such as double knit fabrics, present the most serious problems, due primarily to the relatively large gradient of porosity which exists at different angular orientations thereof and to the relatively glossy fiber surfaces which produce nonrandom specular light at angles other then expected angles of specular reflection from the surface of the material.

Fabrics consist of a plurality of thread extending in a longitudinal direction, commonly called the warp, and a plurality of laterally extending threads, commonly called the woof or weft. Some fabrics, however, have a more complex structure then a simple warp and weft, such as double knit fabrics. These fabrics exhibit a venetian blind effect in which the light transmission through the fabric and, therefore, the light reflectance of the fabric varies in accordance with the angular displacement of a light source from a line which is normal to the fabric surface. It has been found, for example, that many fabrics exhibit a relatively high light transmission when the angle of impinging light rays is 45° with respect to a normal.

Because of the warp and weft of a fabric, the light transmission characteristics thereof vary in accordance with the angular position of such a light source with respect to the warp and weft. That is, if one were to observe the light transmission through a fabric while the fabric is rotated, a gradient of light intensities would be observed which would alternately increase and decrease.

Accordingly, if one of the above mentioned light reflectance instruments is employed to measure the light reflectance from a material having such effects, different readings would be obtained for different angular orientations of the instrument with respect to the material. It can be readily appreciated that such a variation cannot be tolerated. These problems are also enhanced by nonrandom specular light reflected from the relatively glossy surfaces of synthetic threads or fibers. It has been found that light reflectance from fabrics can vary as much as 5% because of the above mentioned effects.

The variation in random specular light in accordance with the orientation of the light source and sensing unit to the material under investigation can be reduced by decreasing the size of the sensing area. However, because of the different types of individual components forming the heterogeneous surface of a material, a relatively small sensing area in the order of several fiber diameters will not produce uniform results at various locations on the same material. Accordingly, a relatively large sensing area must be employed such that the diffused and specular light from all of the different types of individual components forming the heterogeneous surface will be integrated.

It has also been found that doubling the number of light sources will not overcome the above mentioned problems, since diametrically opposed illuminating or sensing positions with respect to the sensing area will each have the same results. Accordingly, it can be appreciated that a need exists for an instrument which is not sensitive to the above mentioned effects. Because of the relatively large sensing area required for materials having a heterogeneous surface configuration, these effects cannot be completely eliminated without complex and expensive optical techniques. However, it has been found that these effects can be reduced with relatively uncomplicated and inexpensive optical techniques to such an extent that they are negligible and with reasonable limits for all practical purposes.

SUMMARY OF THE INVENTION

Accordingly, it is a primary object of the present invention to provide an instrument for measuring light reflectance from the surface of a material having a heterogeneous surface configuration.

A related object of the present invention is to provide an instrument for measuring light reflectance from a material having a heterogeneous surface configuration which is substantially insensitive to orientation effects of such a material.

A further object of the present invention is to provide an instrument for measuring light reflectance from the surface of a material having a heterogeneous configuration which is substantially insensitive to nonrandom specular light effects from individual components of the heterogeneous surface.

Still another object of the present invention is to provide an instrument for measuring light reflectance from a material having a patterned surface which is insensitive to orientation effects of that pattern.

These and other objects of the present invention are obtained by the provision of an odd numbered plurality of light sources which are mounted at equidistant points around an outer periphery of a light sensor and are further mounted on respective lines which pass through the center of a sensing area, which lines are at an angle from 20° to 40° with respect to a line which is perpendicular to the sensing area.

The invention, however, as well as other objects, features and advantages thereof will be more fully realized and understood from the following detailed description, when taken in conjunction with the accompanying drawings, wherein:

BRIEF DESCRIPTION OF THE DRAWINGS

FIG. 1 is a longitudinal sectional view of an instrument for measuring light reflectance which is con- FIG. 2 is an elevational view of a plurality of light sources employed in the instrument illustrated in FIG. 1.

FIG. 3 is a sectional view of a light sensor unit employed in the instrument illustrated in FIG. 1.

Like reference numerals throughout the various views of the drawings are intended to designate the same elements.

DETAILED DESCRIPTION OF THE PREFERRED EMBODIMENT

With reference to FIG. 1, there is shown an instrument for measuring light reflectance which is constructed in accordance with the principles of the present invention. As shown therein, the instrument includes a housing 10 having an aperture 12 in a lower wall thereof which defines a sensing area on a material 14 which is under investigation. Suspended from a top wall of the housing 10 is an illuminating and light sensing unit, generally designated with reference numeral 16. The unit 16 includes a light sensor 18 mounted coaxially with respect to the aperture 12 and illustrated in greater detail in FIG. 3. The unit 16 also includes three light sources 20, 22 and 24 which are mounted at equidistant points around an outer periphery of the sensor 18. The light sources 20, 22 and 24 are also mounted on lines which intersect a center of the aperture 12, at the sensing area, which lines are at an angle of from 20° to 40° with respect to a normal through the center of the sensing area. In a preferred embodiment of the present invention, these lines are at an angle of 30° with respect to that normal.

As mentioned above, the fabric 14 may have a venetian blind effect to the transmission and reflectance of light impinging thereon. Such a venetian blind effect generally occurs when the light rays impinging thereon are at an angle of 45° with respect to a line which is normal thereto. Rotation of the material 14 around such a normal line produces a gradient of light transmission and reflection which is most pronounced at the above mentioned angle at which the venetian blind effect occurs. However, when a light source is mounted at 30° with respect to the normal, the venetian blind effect is substantially reduced.

The provision of an odd number of light sources, such as 3 in the exemplified embodiment of the present invention, at equidistant points around an outer periphery of the sensor 18 further reduces the venetian blind effect and angular orientation effects. That is, the summation of the reflected light, because of the cosine contribution of each component, produces a more uniform reflectance from the sensing area of the material 14. Furthermore, it is believed that the effect of nonrandom specular light from individual fiber surfaces is reduced because of the integration of the light from the three light sources 20, 22 and 24 which impinges on the material 14 and is reflected to the sensor 18. Although it is believed that a toroidal light source surrounding the light sensor 18 would further reduce these effects, such a light source would require relatively complex and expensive optical elements to achieve substantially the same result. The present invention, however, produces light reflectance from the heterogeneous surface which varies no more than 0.02% with variations in the angular position of the instrument of the present invention around a normal to the material 14. Since this amount of variation in the total light reflectance is substantiallly negligible, further reductions in the above mentioned effects at a considerable cost is not practical. It can be appreciated, however, that the present invention reduces the nonuniformity in the light reflectance over prior known devices by a factor of 250.

The light sensor 18 is illustrated more clearly in FIG. 3 and includes a housing 26 which is preferably formed of a heat conducting material, such as aluminum. A photoelectric cell 28 is mounted in the housing 26 and a plurality of optical filters 30, 32 and 34 are mounted at an opening of the housing 26 to provide the desired color bandpass for the photoelectric cell 28. The filters 30, 32 and 34 provide a bell shaped transmission characteristic, typically beginning at the blue spectrum, peaking at the green spectrum, and ending at the red spectrum. A heater transistor 36 is mounted on a wall of the housing 26 and in good heat conducting relationship therewith and a thermistor 38 is embedded therein.

The thermistor 38 is connected in a bridge network having its output connected through an amplifier to the base of the transistor 36. Accordingly, variations in the resistance of the thermistor 38 are reflected in the base drive to the transistor 36 and, therefore, in its conduction level. The conduction level of the transistor 36 establishes the amount of heat generated thereby and supplied to the housing 26. Accordingly, the circuit maintains the housing 26 at a constant temperature.

The temperature stabilized photoelectric cell 28 is connected through an amplifier to a pair of normally open first and second switches. The other side of the first switch is connected to a sample and hold circuit such as a capacitor which, when the first switch is closed, develops a voltage thereon which is proportional to the voltage developed by the photoelectric cell 28 in response to light impinging thereon. The voltage developed on the capacitor is supplied directly to one input of a first comparison circuit and through a first voltage divider to one input of a second comparison circuit.

The other side of the second switch is connected directly to a second input of the second comparison circuit and through a second voltage divider to a second input of the first comparison circuit.

In use, the instrument illustrated in FIG. 1 is placed on a reference material and the first switch is momentarily closed to develop a voltage on the capacitor which is proportional to the amount of light reflectance from that reference material. The voltage divider is a relatively high impedance circuit, such that the voltage developed on the capacitor will not degrade over a period of time corresponding to the amount of time required to perform an operation. Thereafter, the instrument illustrated in FIG. 1 is placed on a second material which is to be matched in its light reflectance qualities with the reference material. The second switch is then closed and a comparison is made in each of the first and second comparator circuits.

The voltage dividers reduce the amplitude of the voltage supplied to each by a predetermined factor, such as by 10%. If the output of the amplifier is higher than the voltage developed by the first voltage divider, an output will be provided on a first line from the second comparison circuit. Also, if the voltage developed on the capacitor is greater then the voltage supplied by the second voltage divider, an output will be provided on a second line from the first comparison circuit. If neither one of the above conditions exist, such outputs will not be generated.

The first and second lines are connected to respective inputs of an AND gate having its output connected through a first indicator light to ground potential. The output of the AND gate is also connected through an inverter and a second indicator light to ground potential. Accordingly, if an acceptable comparison exists, the first indicator light will be illuminated to indicate that the two materials are within a predetermined range of light reflectance with respect to one another. In the above example, such an acceptable comparison would exist when the light reflectance of one material is within plus or minus 10% of the light reflectance of the other material. However, if such an acceptable comparison does not exist, the second indicator light will be illuminated.

It can be readily appreciated that such comparison of the light reflectance of two materials cannot be accurate within reasonable limits if the light reflectance instrument is sensitive to the adverse effects mentioned above. That is, if the instrument is subject to such adverse effects, its orientation with respect to the reference material and the material to be matches thereto may cause a 5% variation in the amount of light reflectance which is sensed. Since it is often desirable to match the two different materials within a range of plus or minus ½%, such a 5% variation would be intolerable. Accordingly, it can be appreciated that the light reflectance instrument of the present invention reduces the effects of the above mentioned problems which are encountered in prior known light reflectance instruments to a practical and negligible amount without expensive and complicated optical elements.

The invention claimed is:

1. An instrument for measuring the light reflectance from fabric and the like materials which have a heterogeneous surface configuration, comprising:
 a housing having a nonreflective interior surface, said housing including a plate having an aperture defining a sensing area, said plate being disposed for engaging the surface of such a material and framing a portion of the material in the aperture, the aperture being sufficient to frame a relatively large number of all of the different types of individual components of the heterogeneous surface in the sensing area;
 a light sensor mounted within said housing coaxially with respect to said aperture and a predetermined distance therefrom; and
 only an odd number of light sources mounted within said housing at equidistant points around an outer periphery of said sensor and providing light beams along respective lines which pass through the center of said aperture, said lines being disposed at an angle with respect to said aperture axis which lies outside the range of from 35° to 55°.

2. The instrument of claim 1, wherein said lines are at an angle of from 25° to 35° with respect to the aperture axis.

3. The instrument of claim 1, wherein said lines are at an angles of 30° with respect to the aperture axis.

4. The instrument of claim 1, wherein said odd number is equal to three.

5. The instrument of claim 4, wherein said lines are at an angle of from 25° to 35° with respect to the aperture axis.

6. The instrument of claim 4, wherein said lines are at an angle of 30° with respect to the aperture axis.

7. The instrument of claim 1, wherein means are provided to maintain said light sensor at a constant predetermined temperature.

* * * * *